United States Patent
Maskara et al.

(10) Patent No.: US 9,138,199 B2
(45) Date of Patent: Sep. 22, 2015

(54) METHOD AND APPARATUS FOR DETECTING SUBAUDIBLE CARDIAC VIBRATIONS

(71) Applicant: Cardiac Pacemakers, Inc., St. Paul, MN (US)

(72) Inventors: Barun Maskara, Blaine, MN (US); Qi An, Blaine, MN (US); Pramodsingh Hirasingh Thakur, Woodbury, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 29 days.

(21) Appl. No.: 14/083,925

(22) Filed: Nov. 19, 2013

(65) Prior Publication Data

US 2014/0155762 A1    Jun. 5, 2014

Related U.S. Application Data

(60) Provisional application No. 61/779,021, filed on Mar. 13, 2013, provisional application No. 61/732,627, filed on Dec. 3, 2012.

(51) Int. Cl.
*A61B 5/02* (2006.01)
*A61B 7/04* (2006.01)
*A61B 7/00* (2006.01)
*A61B 5/0205* (2006.01)
*A61B 5/0408* (2006.01)

(52) U.S. Cl.
CPC . *A61B 7/04* (2013.01); *A61B 7/003* (2013.01); *A61B 5/02* (2013.01); *A61B 5/0205* (2013.01); *A61B 5/0408* (2013.01)

(58) Field of Classification Search
CPC ............ A61B 7/02; A61B 7/026; A61B 7/04; A61B 7/045; A61B 7/003; A61B 5/02; A61B 5/0205; A61B 5/0408
USPC .......................................... 600/508, 528, 527
See application file for complete search history.

(56) References Cited

U.S. PATENT DOCUMENTS

| | | | |
|---|---|---|---|
| 5,218,969 A * | 6/1993 | Bredesen et al. | 600/523 |
| 6,726,635 B1 | 4/2004 | LaSala | |
| 7,431,699 B2 | 10/2008 | Siejko et al. | |
| 2001/0030077 A1 * | 10/2001 | Watson | 181/131 |

OTHER PUBLICATIONS

Johnston, Franklin D, et al., "Vibrations of Low Frequency Over the Precordium", Circulation: vol. III, Apr. 1951, 579-588.

* cited by examiner

*Primary Examiner* — Christopher D Koharski
*Assistant Examiner* — Michael Carey
(74) *Attorney, Agent, or Firm* — Schwegman Lundberg & Woessner

(57) ABSTRACT

A monitoring system senses a physiological signal indicative of mechanical vibrations including audible and/or subaudible frequency ranges and presents information related to the physiological signal to a user. The presented information includes subaudible components of the physiological signal. In various embodiments, the information can be presented as a visual signal representing the mechanical vibrations including the subaudible components, an audial signal representing the mechanical vibrations having a spectrum shifted to an audible frequency range, and/or an audial signal representing the mechanical vibrations having a spectrum compressed into an audible frequency range. An example of the physiological signal can include a heart sound signal indicative of heart sounds including cardiac mechanical vibrations in audible and subaudible frequency ranges.

20 Claims, 5 Drawing Sheets

METHOD AND APPARATUS FOR DETECTING SUBAUDIBLE CARDIAC VIBRATIONS

CLAIM OF PRIORITY

This application claims the benefit of priority under 35 U.S.C. §119(e) of U.S. Provisional Patent Application Ser. No. 61/779,021, filed on Mar. 13, 2103, and U.S. Provisional Patent Application Ser. No. 61/732,627, filed on Dec. 3, 2012, each of which is herein incorporated by reference in its entirety.

TECHNICAL FIELD

This document relates generally to cardiac diagnostic systems and particularly to a system that senses signals indicative of cardiac mechanical vibrations (heart sounds) and detects specified-type cardiac mechanical vibrations including their components in the subaudible frequency range.

BACKGROUND

The heart is the center of a person's circulatory system. It includes a complex electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. These mechanical pumping functions are accomplished by contractions of the myocardium (heart muscles). In a normal heart, the sinoatrial (SA) node, the heart's natural pacemaker, generates electrical impulses, called action potentials, that propagate through an electrical conduction system to various regions of the heart to excite myocardial tissues in these regions. Coordinated delays in the propagations of the action potentials in a normal electrical conduction system cause the muscles in various regions of the heart to contract in synchrony such that the pumping functions are performed efficiently. The normal pumping functions of the heart, or the normal hemodynamic performance, require a normal electrical system to generate the action potentials and deliver them to designated portions of the myocardium with proper timing, a normal myocardium capable of contracting with sufficient strength, and a normal electro-mechanical association such that all regions of the heart are excitable by the action potentials.

Electrocardiography (ECG) is known to indicate the functions of the electrical system by allowing monitoring of the action potentials at various portions of the heart. Heart sounds, or generally energies resulted from the heart's mechanical vibrations, indicate the head's mechanical activities. Measurements performed with simultaneously recorded ECG and heart sounds provide for quantitative indications of the electro-mechanical association.

One type of heart sound, known as the third heart sound, or S3, can be used for assessment of heart failure status of a patient. A heart failure patient suffers from an abnormal electrical conduction system with excessive conduction delays and deteriorated heart muscles that result in asynchronous and weak heart contraction, and hence, reduced pumping efficiency, or poor hemodynamic performance. While the ECG of a heart failure patient may show excessive delays and/or blockages in portions of the electrical conduction system, S3 indicates his or her heart's abnormal mechanical functions. For example, an increase in S3 activity is known to be an indication of elevated filing pressures, which may result in a state of decompensated heart failure. Additionally, S3 amplitude is also related to filing pressures of the left ventricle during diastole. The pitch, or fundamental frequency, of S3 is related to ventricular stiffness and dimension. Chronic changes in S3 amplitude are correlated to left ventricular chamber stiffness and degree of restrictive filling. Such parameters indicate abnormal cardiac conditions, including degrees of severity, and need of appropriate therapies.

For these and other reasons, there is a need for detecting S3 in diagnosis, monitoring, and treatment of cardiac conditions including heart failure.

SUMMARY

A system for monitoring a patient and presenting diagnostic information to a user includes a vibration sensor, a processing circuit, and a user interface. The vibration sensor can be configured to sense a physiological signal indicative of mechanical vibrations in a sensing frequency range including audible and subaudible frequency ranges. The processing circuit can be configured to produce one or more presentation signals representing the mechanical vibrations in a presentation frequency range including at least one subaudible frequency range of the sensing frequency range. The user interface can be configured to present the one or more presentation signals to the user. In various embodiments, the one or more presentation signals can include a visual signal representing the mechanical vibrations including subaudible components, an audial signal representing the mechanical vibrations having a spectrum shifted to an audible frequency range, and/or an audial signal representing the mechanical vibrations having a spectrum compressed into an audible frequency range. The user interface can be configured to present the one or more presentation signals to the user.

An example of the physiological signal can include a heart sound signal indicative of heart sounds cardiac including mechanical vibrations in audible and subaudible frequency ranges. In an example, the heart sound signal is indicative of third heart sounds (S3), which includes audible and subaudible components.

This Summary is an overview of some, of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
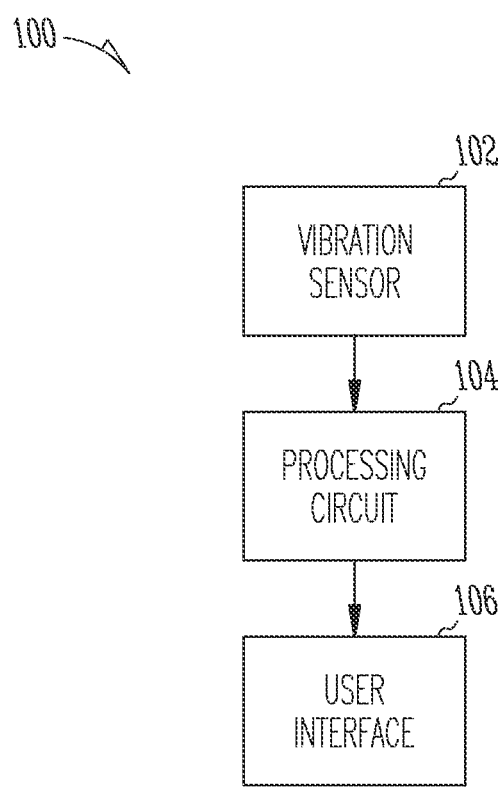
FIG. 1 is a block diagram illustrating an embodiment of a heart sound monitoring system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a system and method for monitoring and analyzing heart sounds, including audible and inaudible (subaudible, as known as infrasonic) cardiac mechanical vibrations that are indicative of a heart's mechanical events related to the heart's pumping functions and hemodynamic performance. The system is used to obtain heart sound related information that allows for diagnosis of cardiac conditions and selection of therapies for preventing and/or treating the cardiac conditions. In one embodiment, the present system is implemented in a form of a stethoscope that allows for detection of inaudible cardiac mechanical vibrations such as components of the third heart sounds (S3) in the subaudible frequency range, as specifically discussed in this document. However, it is to be understood that the present methods and apparatuses may be employed in other types of medical devices, including, but not being limited to, various types of cardiac diagnostic, monitoring, and/or therapeutic devices.

Known and studied heart sounds include the "first heart sound" or S1, the "second heart sound" or S2, the "third heart sound" or S3, the "fourth heart sound" or S4, and their various sub-components. S1 is known to be indicative of among other things, mitral valve closure, tricuspid valve closure, and aortic valve opening. S2 is known to be indicative of, among other things, aortic valve closure and pulmonary valve closure, S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure).

In this document, "heart sound" includes audible and inaudible (subaudible) mechanical vibrations caused by cardiac activity that can be sensed with an accelerometer. In other words, "heart sound" includes cardiac mechanical vibrations in audible and subaudible frequency ranges. Accordingly, when a vibration sensor such as an accelerometer or microphone is used to sense the heart sounds, the scope of energy included in the sensed "acoustic signal" extends to energies associated with such cardiac mechanical vibrations. Unless noted otherwise, S1 refers to the first heart sound, S2 refers to the second heart sound, S3 refers to the third heart sound, and S4 refers to the fourth heart sounds, each as a heart sound type, or as one or more occurrences of the corresponding type heart sounds, depending on the context. A "heart beat" includes a cardiac cycle. An "S3 beat" includes a cardiac cycle during which S3 is detected. An audible heart sound/ audible heart cardiac mechanical vibration refers to heart sound/cardiac mechanical vibration with frequency components in the audible frequency range. A subaudible heart sound/subaudible cardiac mechanical vibration refers to heart sound/cardiac mechanical vibration with frequency components in the subaudible frequency range.

In this document, a "user" includes a physician or other caregiver who examines and/or treats a patient using one or more of the methods and apparatuses reported in the present document.

S3 detection is particularly discussed in this document because the subaudible components of S3 are of interest in, for example, prediction of cardiac events related to heart failure and identification of patients with elevated risk for heart failure. It has been learned that S3 may have more energy distributed in the subaudible range than in the audible range. Consequently, S3 detection from signals including subaudible components of S3 may be for valuable in providing diagnostic information related to heart failure than S3 detection from signals including only audible components of S3. However, the subaudible components of S3 cannot be heard using a conventional acoustic stethoscope. The present method and apparatus provides for one or more user-perceivable signals representing audible and subaudible components of S3. While S3 is discussed as a specific example, the present subject matter can be applied in monitoring other vibrations of the heart or other body organs that include subaudible components.

FIG. 1 is a block diagram illustrating an embodiment of a heart sound monitoring system 100. System 100 includes a vibration sensor 102, a processing circuit 104, and a user interface 106.

Vibration sensor 102 is configured to sense a heart sound signal indicative of heart sounds. The heart sounds include cardiac mechanical vibrations in a sensing frequency range including audible and subaudible frequency ranges. In one embodiment, vibration sensor 102 has a sensing frequency range such that the sensed heart sound signal is indicative of at least S3, including audible S3 components and subaudible S3 components. In various embodiments, vibration sensor 102 is any sensor that is capable of sensing mechanical vibrations in audible and subaudible frequency ranges. Examples of vibration sensor 102 include an accelerometer or a microphone. An accelerometer (or accelerometer type sensor) directly picks up vibrations or accelerations associated with sound. A microphone (or phonogram type sensor) has a diaphragm which "vibrates" in response to pressure waves associated with sound. Such vibration sensors transduce the mechanical vibrations in audible and subaudible frequency range into an electrical signal.

Processing circuit 104 is configured to process the sensed heart sound signal to produce one or more presentation signals. The one or more presentation signals represent the heart sounds in a presentation frequency range including at least one subaudible frequency range of the sensing frequency range. The presentation frequency range is set to a range for presenting types of heart sound of interest. For example, the presentation frequency range can be set to the frequency range of S3 such that system 100 is an S3 monitoring system.

User interface 106 is configured to present the one or more presentation signal to the user. In various embodiments, the one or more presentation signals include one or more of audial and/or visual signals. In one embodiment, user interface 106 allows the user to specify the presentation frequency range or enter a command specifying the frequency range. For example, an "S3" command may be entered to set the presentation frequency range to the frequency range of S3, when the patient is suspected to be experiencing heart failure or have an elevated risk for heart failure.

The one or more presentation signal when presented by user interface 106 are each directly perceivable to the user (assuming that the user has normal vision and hearing or uses appropriate visional and/or hearing corrective means). In one embodiment, the one or more presentation signals when combined represent the heart sounds in the presentation frequency range. In another embodiment, the one or more presentation signals each represent the heart sounds in the presentation frequency range.

In various embodiments, the circuit of system 100, including its various elements discussed in this document, is implemented using a combination of hardware and software. In various embodiments, processing circuit 104, including their various elements discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

In various embodiments, system 100 can be used to monitor any physiological signal indicative of mechanical vibrations of in a patient's body in a sensing frequency range including audible and/or subaudible frequency ranges, with S3 discussed in this document as only a specific example of such a physiological signal. Other examples of such a physiological signal can include gastric/intestinal motility sounds, lung sound, breath sounds, and respiratory auscultation. Vibration sensor 102 can be configured to sense the physiological signal. Processing circuit 104 can be configured to process the sensed physiological signal to produce the one or more presentation signals. User interface 106 can be configured to present the one or more presentation signal to the user.

Figure 2:
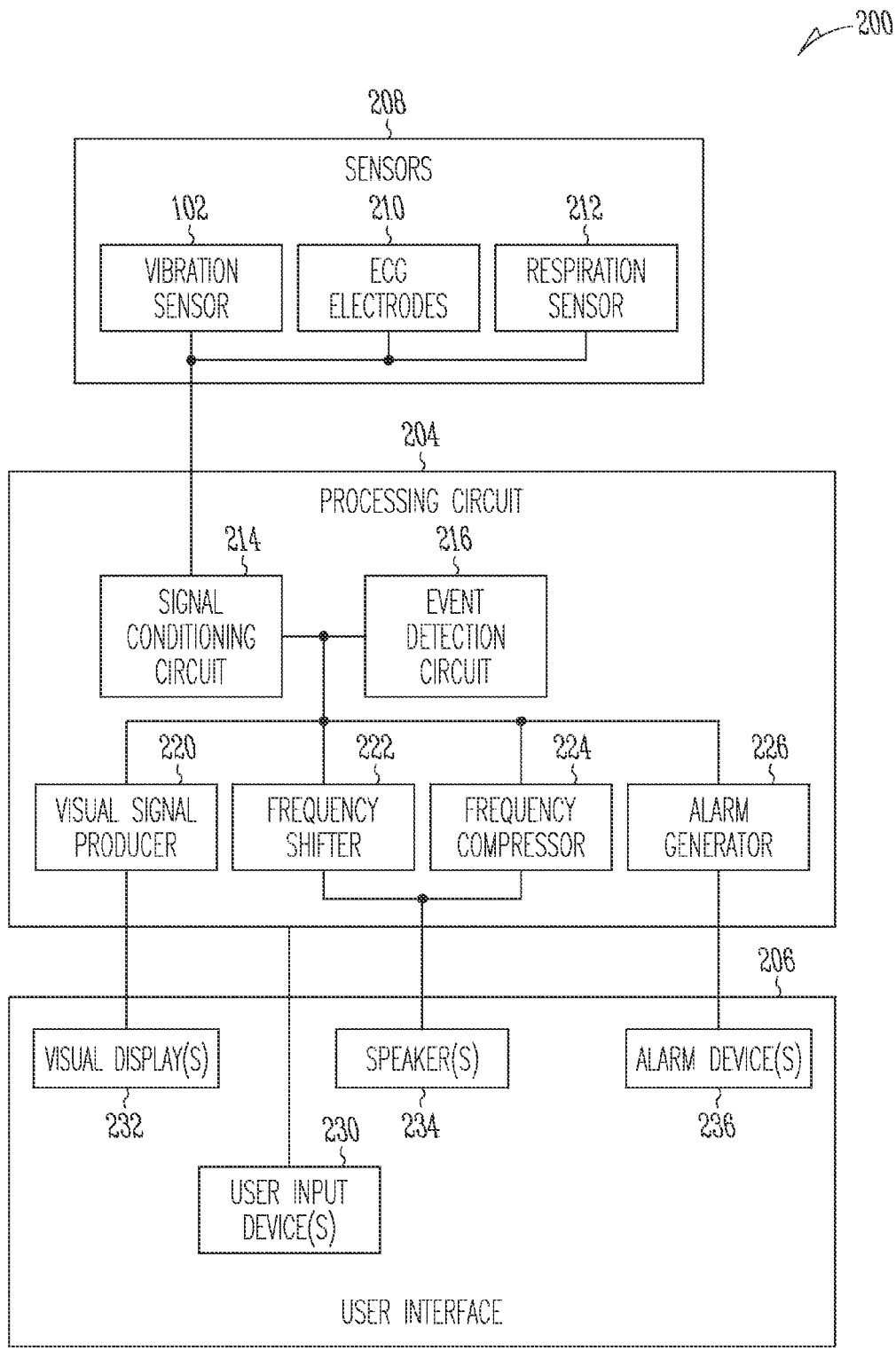
FIG. 2 is a block diagram illustrating another embodiment of the heart sound monitoring system.

FIG. 2 is a block diagram illustrating an embodiment of a heart sound monitoring system 200. System 200 represents an embodiment of system 100 and includes sensors 208, a processing circuit 204, and a user interface 206.

Sensors 208 are configured to sense one or more physiological signals. In the illustrated embodiment, sensors 208 include vibration sensor 102, electrocardiographic (ECG) electrodes 210, and a respiratory sensor 212. ECG electrodes 210 allow for sensing of one or more ECG signals. Respiratory sensor 212 is configured to sense one or more respiratory signals each indicative of respiratory cycles. In one embodiment, respiratory sensor 212 includes an impedance sensor to sense an impedance signal indicative of the respiratory cycles. In various embodiments, sensors 208 may include vibration sensor 102 alone, vibration sensor 102 and either or both of ECG electrodes 210 and respiratory sensor 212, or vibration sensor 102, either or both of ECG electrodes 210 and respiratory sensor 212, and one or more additional sensors useful in monitoring and/or analysis of the heart sounds and/or other conditions of the patient.

Processing circuit 204 represents an embodiment of processing circuit 104. In the illustrated embodiment, processing circuit 204 includes a signal conditioning circuit 214, an event detection circuit 216, a visual signal producer 220, a frequency shifter 222, a frequency compressor 224, and an alarm generator 226. In various embodiments, processing circuit 204 may include signal conditioning circuit 214, optionally event detection circuit 216, and any one or more of the visual signal producer 220, frequency shifter 222, frequency compressor 224, and alarm generator 226, depending on the desirable format of presenting the one or more presentation signals.

Signal conditioning circuit 214 is configured to condition sensor signals produced by sensors 208. In various embodiments, signal conditioning circuit 214 conditions the heart sound signal sensed by vibration sensor 102, such as by filtering the heart sound signal using cutoff frequencies of a processing frequency range and amplifying the filtered heart sound signal. In one embodiment, signal conditioning circuit 214 conditions the heart sound signal using the other one or more physiological signals sensed by sensors 208, such as to enhance the heart sounds to facilitate their detection. In one embodiment, signal conditioning circuit 214 is configured to perform ensemble averaging of the heart sound signal using an ECG signal sensed using ECG electrodes 210. In another embodiment, signal conditioning circuit 214 is configured to gate the heart sound signal using a respiratory signal sensed using respiration sensor 212.

Event detector 216 is configured to detect specified events from the one or more physiological signals sensed using sensors 208. In various embodiments, event detector 216 is configured to detect specified one or more types of heart sounds using the sensed and conditioned heart sound signal. In various embodiments, event detector 216 is configured to detect specified one or more types of cardiac events from the one or more ECG signals and/or one or more types of respiratory events from the one or more respiratory signals for use in enhancement of detection of the specified one or more types of heart sounds. For example, a cardiac signal recurring in each cardiac cycle can be detected for use in the ensemble averaging of the heart sound signal, a respiratory phase such as inspiration phase or expiration phased can be detected for gating the heart sound signal, and various cardiac events and/heart sounds can be used to set windows for detection of other heart sounds. In one embodiment, event detection circuit 216 is configured to detect S1, S2, and/or S3. An example of such a heart sound detector is discussed in U.S. Pat. No. 7,431,699, entitled "METHOD AND APPARATUS FOR THIRD HEART SOUND DETECTION," filed on Dec. 24, 2003, assigned to Cardiac Pacemakers, Inc., the specification of which is incorporated herein by reference in its entirety. In one embodiment, event detection circuit 216 is configured to detect S1, S2, S3, and/or S4. In one embodiment, event detection circuit 216 is configured to produce event markers for each detected heart sound. In one embodiment, event detection circuit 216 is configured to detect specified type characteristics of the heart sound signal associated with one or more types of the detected heart sounds. In one embodiment, S3 is detected, and an S3 marker is produced to be associated with each detected occurrence of S3. In one embodiment, specified type characteristics of the heart sound signal associated with S3 are detected. In one embodiment, event detection circuit 216 is configured to detect one or more specified types of alarming events. Example of such alarming events include detection of S3, repeated detections of S3 (e.g., when the repetition exceeds a specified threshold), or an S3 index (or prevalence, which a ratio of the number of heart beats during which S3 are detected to the number of all the heart beats during a detection period) exceeding a specified threshold, as such events may be associated with heart failure or elevated risk for heart failure.

Visual signal producer 220, frequency shifter 222, frequency compressor 224, and alarm generator 226 are each configured to produce a presentation signal representing the heart sounds having subaudible components. Visual signal producer 220 is configured to produce a visual signal representing the heart sound signal in the presentation frequency range. In one embodiment, visual signal producer 220 is set to the presentation frequency range such that the visual signal is indicative of at least S3 including the subaudible S3 components.

Frequency shifter 222 is configured to produce an audial signal by shifting the heart sound signal in the presentation frequency range to an audible frequency range, when the presentation frequency range includes subaudible frequencies. One embodiment, frequency shifter 222 is configured to produce the audial signal to be indicative of at least S3 including the subaudible S3 components. In one embodiment, frequency shifter 222 includes a circuit that electronically shifts the frequency. In another embodiment, frequency shifter 222 includes a structure that mechanically shifts the frequency.

Frequency compressor 224 is configured to produce an audial signal by compressing the heart sound signal in the presentation frequency range to an audible frequency range, when the presentation frequency range includes subaudible frequencies. In one embodiment, frequency compressor 224 is configured to produce the audial signal to be indicative of at least S3 including the subaudible S3 components. In one embodiment, frequency compressor 224 includes a circuit that electronically compresses the frequency. In another embodiment, frequency shifter 222 includes a structure that mechanically compresses the frequency.

Alarm generator 226 is configured to generate one or more alert and/or alarm signals in response to a detection of the one or more specified types of alarming events. The one or more alert and/or alarm signals may each be an audial signal or a visual signal that informs the user of a patient condition that requires attention from the user. In various embodiments, alarm generator 226 is configured to generate one or more alert signals and one or more alarming signals each as a function of a type and/or severity of an alarming event. For example, an alarming signal may be associated with an event that has a higher degree of severity and requires more immediate attention by the user than an event associated with an alert signal. In one embodiment, alarm generator 226 is configured to generate a plurality of alert and/or alarming signals that correspond to a plurality of alarming events with different levels of severity and urgency for medical attention.

User interface 206 represents an embodiment of user interface 106 and is configured to present the one or more presentation signal to the user. In the illustrated embodiment, user interface 206 includes one or more user input devices 230, one or more visual displays 232, one or more speakers 234, and one or more alarm devices 236. In various embodiments, user interface 206 may include any one or combination of one or more user input devices 230, one or more visual displays 232, one or more speakers 234, and one or more alarm devices 236. User input device(s) 230 receive commands from the user to control operation of system 200. Examples of user input device(s) 230 includes one or more of a power switch for turning system 200 on and off and a device for receiving a command specifying at least the presentation frequency range (such as by selecting one or more types of heart sounds). Visual display(s) 232 are configured to display the visual signal produced by visual signal producer 220. Examples of visual display(s) 232 include light-emitting diode (LED), LED array, and liquid crystal display (LCD). Speaker(s) 234 are configured to transmit the audible signal produced by frequency shifter 222 or frequency compressor 224. Alarm device(s) 236 are configured to present the one or more alarm signals produced by alarm generator 226. In one embodiment, alarm device(s) 236 include at least one of visual display(s) 232 and speaker(s) 234. The one or more alarm signals may each be an audial signal or a visual signal that is directly perceivable by the user when presented by alarm device(s) 236.

Figure 3:
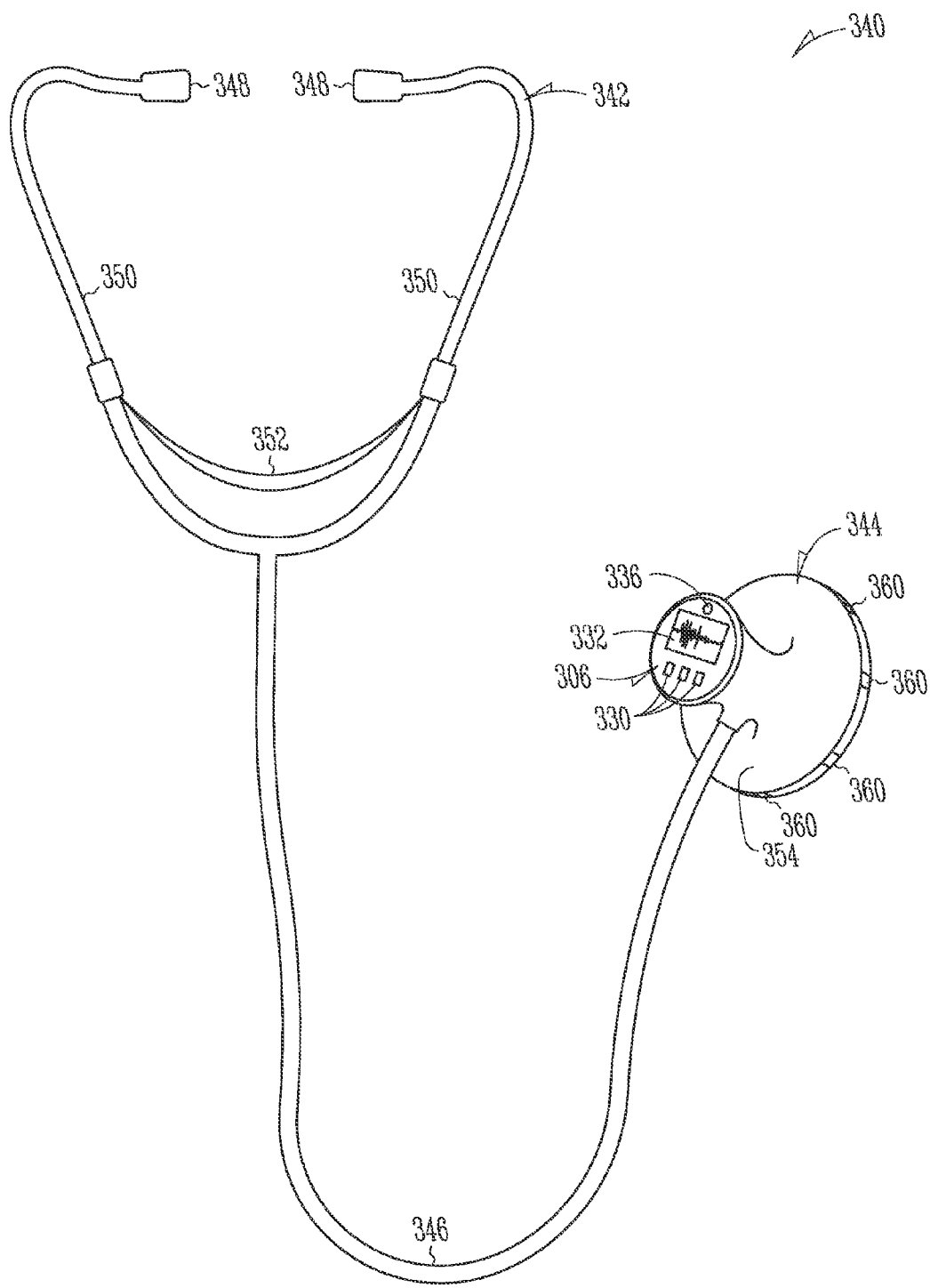
FIG. 3 is an illustration of an embodiment of a stethoscope including the heart sound monitoring system.

FIG. 3 is an illustration of an embodiment of a stethoscope 340 including system 100 or 200. Stethoscope 340 includes a headset 342, a chest piece 344, and tubing 346 coupled between headset 342 and chest piece 344. Headset 342 includes ear tips 348, ear tubes 350, and tension springs 352. Chest piece 344 includes a housing 354 containing portions of system 100 or 200. A user interface 306 represents an embodiment of user interface 206 and is at least partially integrated into or mounted onto housing 354. In the illustrated embodiment, user interface 306 includes user input devices 330, a visual display 332, and an alarm device 336. Visual display 332 is mounted onto the side of chest piece 344 opposite to the side that is to be placed on the surface of a patient to hear the patient's heart sounds.

In various embodiments, system 100 or 200 is distributed in stethoscope 340 in any suitable way as understood by those skilled in the art. For example, a major portion, or substantially the entirety, of system 100 or 200 can be included in chest piece 344. In one embodiment, speaker(s) 234 are contained in housing 354, and the audible signal(s) are acoustically transmitted to ear tips 348 through tubing 346 and ear tubes 350. In another embodiment, speaker(s) 234 are contained ear tips 348 and electrically connected to processing circuit 204 via wires running within tubing 346 and ear tubes 350.

Figure 4:
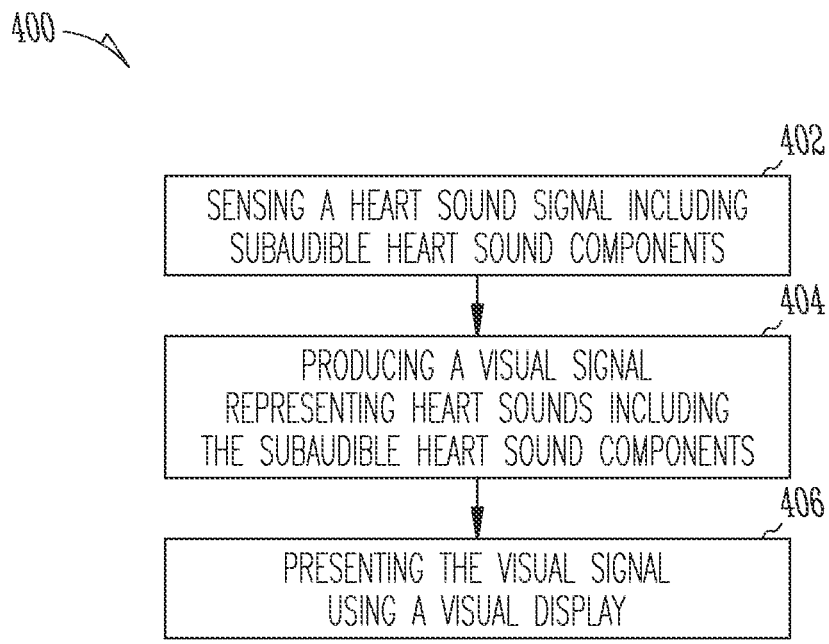
FIG. 4 is a flow chart illustrating an embodiment of a method for monitoring and presenting heart sounds.
Figure 5:
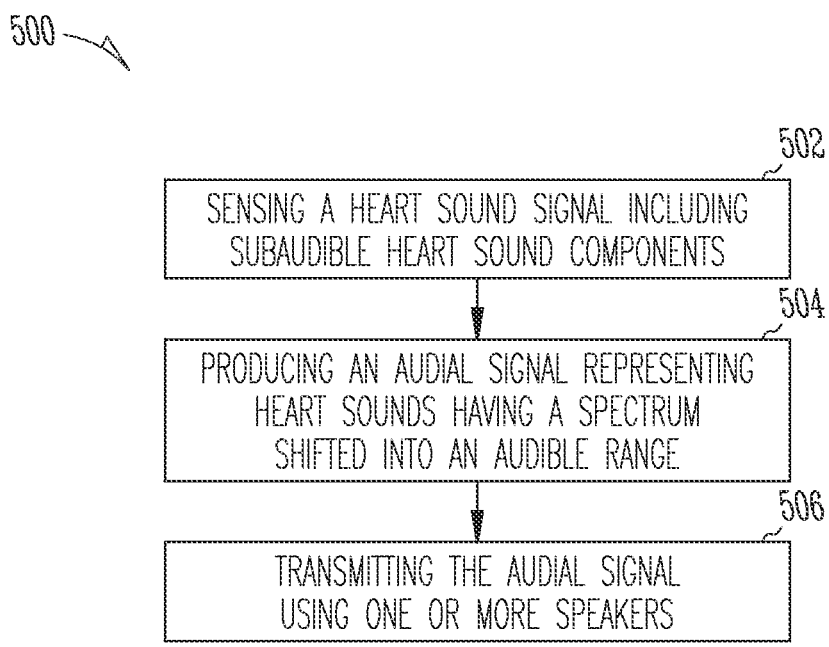
FIG. 5 is a flow chart illustrating an embodiment of another method tier monitoring and presenting heart sound.
Figure 6:
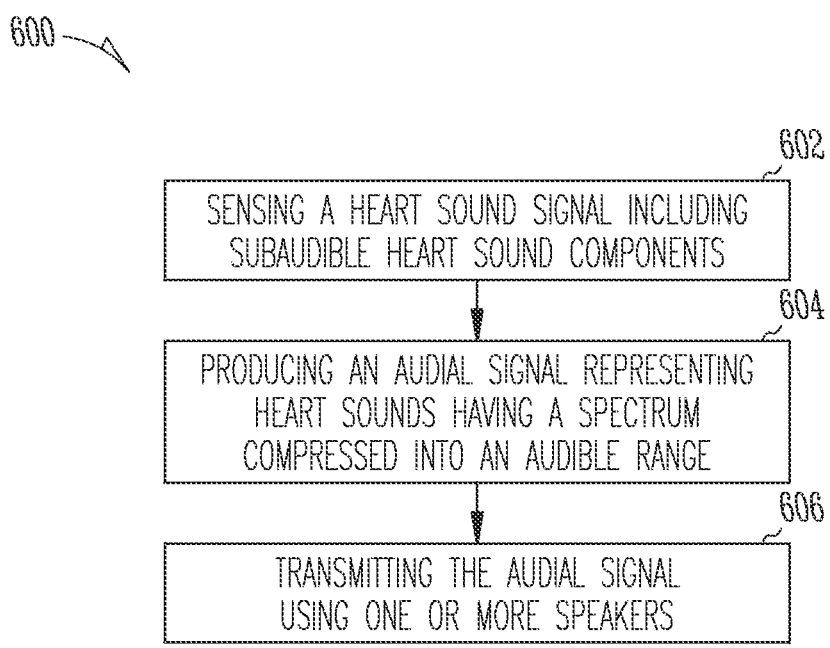
FIG. 6 is a flow chart illustrating an embodiment of another method for monitoring and presenting heart sound.

FIGS. 4-6 are flow charts illustrating various methods for monitoring and presenting S3. In various embodiments, these methods are each performed using an electronic stethoscope such as stethoscope 340. In various other embodiments, these methods are each performed using system 100 or 200 as part of a medical monitoring, diagnostic, and/or therapeutic device or system, such as a system for heart failure patient management. In various embodiments, these methods are applied for monitoring and presenting S3, including audible S3 components and subaudible S3 components. The methods discussed with references to FIGS. 4-6 can be applied to monitor any physiological signal indicative of mechanical vibrations of in a patient's body in a sensing frequency range including audible and/or subaudible frequency ranges, with S3 specifically discussed as only an example of such a physiological signal.

FIG. 4 is a flow chart illustrating an embodiment of a method 400 for monitoring and presenting heart sounds. At 402, a heart sound signal indicative of heart sounds is sensed. The heart sounds includes cardiac mechanical vibrations in a sensing frequency range including audible and subaudible frequencies. At 404, a visual signal representing the heart sounds in a presentation frequency range is produced. The presentation frequency range includes at least one subaudible frequency range of the sensing frequency range. In various embodiments, the visual signal is produced using the heart sound signal that has been filtered and amplified. In one embodiment, the heart sound signal has been ensemble averaged when being used to produce the visual signal. At 406, the visual signal is presented to the user using a visual display. In various embodiments, the visual signal may include waveform of the heart sound signal, isolated waveform associated with one or more specified types of heart sounds, event markers associated with the one or more specified types of heart sounds, and/or detected characteristics of the heart sound signal associated with the one or more specified types of heart sounds. In one embodiment, the one or more specified types of heart sounds include S3.

FIG. 5 is a flow chart illustrating another embodiment of a method 500 for monitoring and presenting heart sounds. At 502, a heart sound signal indicative of heart sounds is sensed. The heart sounds includes cardiac mechanical vibrations in a sensing frequency range including audible and subaudible frequencies. At 504, an audial signal representing the heart sounds is produced by shifting the spectrum of the heart sounds to an audible frequency range. In various embodiments, the audial signal is produced using the heart sound signal that has been filtered and amplified. In one embodiment, the heart sound signal has been ensemble averaged when being used to produce the audial signal. At 506, the audible signal is transmitted to the user using one or more speakers. The transmitted audial signal represents the heart sounds including subaudible components.

FIG. 6 is a flow chart illustrating another embodiment of a method 600 for monitoring and presenting heart sounds. At 602, a heart sound signal indicative of heart sounds is sensed. The heart sounds includes cardiac mechanical vibrations in a sensing frequency range including audible and subaudible frequencies. At 604, an audial signal representing the heart sounds is produced by compressing the spectrum of the heart sounds to an audible frequency range. In various embodiments, the audial signal is produced using the heart sound signal that has been filtered and amplified. In one embodiment, the heart sound signal has been ensemble averaged when being used to produce the audial signal. At 606, the audible signal is transmitted to the user using one or more speakers. The transmitted audial signal represents the heart sounds including subaudible components.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the fill scope of equivalents to which such claims are entitled.

What is claimed is:

1. A system for monitoring a patient and presenting diagnostic information to a user, the system comprising:
   a vibration sensor configured to sense a physiological signal indicative of mechanical vibrations in a sensing frequency range including audible and subaudible frequency ranges;
   a further sensor configured to sense a further physiological signal;
   a processing circuit coupled to the vibration sensor, the processing circuit configured to produce one or more presentation signals representing the mechanical vibrations in a presentation frequency range including at least one subaudible frequency range of the sensing frequency range using the physiological signal and the further physiological signal; and
   a user interface coupled to the processing circuit, the user interface configured to present the one or more presentation signals to the user,
   wherein the further sensor includes electrocardiographic electrodes configured to sense an electrocardiographic signal, and the processing circuit includes a signal conditioning circuit configured to perform ensemble averaging of the heart sound signal using the ECG signal.

2. The system of claim 1, comprising a stethoscope including the vibration sensor, the processing circuit, and the user interface, wherein the processing circuit comprises a visual signal producer configured to produce a visual signal of the one or more presentation signals, and the user interface comprises a visual display configured to display the visual signal.

3. The system of claim 2, wherein the user interface comprises a user input device configured to receive a command specifying the presentation frequency range.

4. The system of claim 2, wherein the visual signal producer is configured to produce the visual signal in the presentation frequency range such that the visual signal is indicative of at least third heart sound (S3) including the subaudible S3 components.

5. The system of claim 1, wherein the physiological signal comprises a heart sound signal indicative of cardiac mechanical vibrations, and the presentation frequency range is programmed to cover a frequency range of third heart sound (S3).

6. The system of claim 5, wherein the further comprising a respiratory sensor configured to sense a respiratory signals indicative of respiratory cycles, and the processing circuit comprises a signal conditioning circuit configured to gate the heart sound signal using the respiratory signal.

7. A system for monitoring a patient and presenting diagnostic information to a user, the system comprising:
   a vibration sensor configured to sense a heart sound signal indicative of cardiac mechanical vibrations in a sensing frequency range including audible and subaudible frequency ranges;
   a processing circuit coupled to the vibration sensor, the processing circuit configured to produce one or more presentation signals representing the mechanical vibrations in a presentation frequency range including at least one subaudible frequency range of the sensing frequency range using the physiological signal and the further physiological signal; and
   a user interface coupled to the processing circuit, the user interface configured to present the one or more presentation signals to the user,
   wherein the presentation frequency range is programmed to cover a frequency range of third heart sound (S3), the processing circuit comprises an S3 detector configured to detect S3 and an alarm signal generator configured to generate an alert or alarm signal of the one or more presentation signals in response to the detection of S3, and the user interface comprises an alarm device configured to present the alert or alarm signal to the user.

8. The system of claim 1, wherein the processing circuit comprises a frequency shifter configured to produce an audial signal of the one or more presentation signals by shifting the physiological signal in the presentation frequency range to an audible frequency range, and the user interface comprises one or more speakers configured to transmit the audial signal.

9. The system of claim 1, wherein the processing circuit comprises a frequency compressor configured to produce an audial signal of the one or more presentation signals by compressing the physiological signal in the presentation frequency range into an audible frequency range, and the user interface comprises one or more speakers configured to transmit the audial signal.

10. A patient monitoring method, comprising:
    sensing a heart sound signal using a vibration sensor of an electronic stethoscope, the heart sound signal indicative of mechanical vibrations in a sensing frequency range including audible and subaudible frequency ranges;
    sensing an electrocardiographic (ECG) signal using ECG electrodes of the electronic stethoscope;

ensemble averaging the heart sound signal using the ECG signal using a processing circuit of the electronic stethoscope;

producing one or more presentation signals representative of the mechanical vibrations in a presentation frequency range including at least one subaudible frequency range of the sensing frequency range using the ensemble averaged heart sound signal using the processing circuit of the electronic stethoscope; and presenting the one or more presentation signals using a user interface of the electronic stethoscope.

11. The method of claim 10, wherein sensing the heart sound signal using the vibration sensor comprises sensing the heart sound signal using an accelerometer.

12. The method of claim 11, wherein producing the one or more presentation signals comprises producing a visual signal representative of the heart sounds in the presentation frequency range, and presenting the one or more presentation signals comprises presenting the visual signal using a visual display of the user interface.

13. The method of claim 12, wherein producing and presenting the visual signal comprises producing and presenting waveform of the heart sound signal.

14. The method of claim 13, wherein producing and presenting the visual signal comprises producing and presenting isolated waveform associated with one or more specified types of heart sounds.

15. The method of claim 14, wherein producing and presenting the visual signal comprises producing and presenting isolated waveform associated with third heart sound (S3).

16. The method of claim 13, wherein producing and presenting the visual signal comprises producing and presenting event markers associated with the one or more specified types of heart sounds.

17. The method of claim 11, wherein producing the one or more presentation signals comprises producing an audial signal representative of the heart sounds, the producing including shifting the spectrum of the heart sounds to an audible frequency range.

18. The method of claim 11, wherein producing the one or more presentation signals comprises producing an audial signal representative of the heart sounds, the producing including compressing the spectrum of the heart sounds to an audible frequency range.

19. The system of claim 7, comprising a stethoscope including the vibration sensor, the further sensor, the processing circuit, and the user interface.

20. The system of claim 19, wherein the processing circuit comprises a visual signal producer configured to produce a visual signal of the one or more presentation signals, and the user interface comprises a visual display configured to display the visual signal.

* * * * *